United States Patent [19]

Shroot et al.

[11] Patent Number: 4,666,941
[45] Date of Patent: May 19, 1987

[54] PHARMACEUTICAL USES OF SUBSTITUTED 6(5,6,7,8)TETRAHYDRO-5,5,8,8-TETRAMETHYL-2-NAPHTHYL)-2-NAPHTHOIC ACID AND ITS ESTERS

[75] Inventors: Braham Shroot, Antibes; Jacques Eustache, Grasse; Martine Bouclier, Antibes, all of France

[73] Assignee: Groupement Economique dit: Centre International de Recherces Dermatologiques C.I.R.D., Valbonne, France

[21] Appl. No.: 675,700

[22] Filed: Nov. 28, 1984

[30] Foreign Application Priority Data

Nov. 28, 1983 [FR] France ................................ 83 18917

[51] Int. Cl.⁴ .................... A61K 31/19; A61K 31/235
[52] U.S. Cl. ................................... 514/569; 514/544; 514/859; 514/863; 560/56; 562/427; 562/467
[58] Field of Search ........................ 560/10, 56, 100; 562/427, 467, 490; 514/544, 569, 859, 863

[56] References Cited

U.S. PATENT DOCUMENTS 4,454,341 6/1984 Dawson et al. .................. 560/100

OTHER PUBLICATIONS

Sani, Brahma P. et al., *Biochem. J.* (1978), vol. 171, pp. 711–716.
Trown, Patrick W. et al., *Cancer Research*, vol. 40 (1980), pp. 212–220.
Strickland, Sidney et al., *Cancer Research*, vol. 43 (1983), pp. 5268–5271.
J. Med. Chem., vol. 26, No. 11, Nov. 11, 1983, pp. 1653–1656, "Synthesis and Pharmacological Activity of 6-[(E)-2-(2,6,6-Trimethyl-1-cyclohexen-lyl)ether-1--yl] and 6-(1,2,3,4-tetrahydro-1,1,4,4-tetramethyl-6-naphthyl)-2-naphthalene caboxylic acids", Dawson et al.

Primary Examiner—Natalie Trousof
Assistant Examiner—L. Hendriksen
Attorney, Agent, or Firm—Cushman, Darby & Cushman

[57] ABSTRACT

New polysubstituted derivatives of naphtalene.
These derivatives correspond to the following formula:

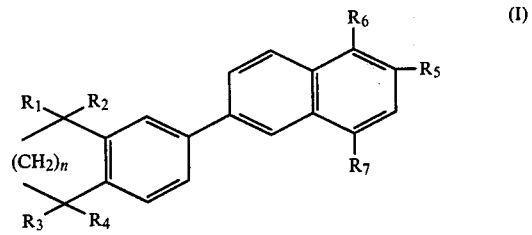

in which:
$R_1$ to $R_4$ is H or $CH_3$
$R_5$ is

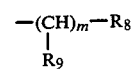

(i)

$-C \equiv N$ (ii)

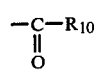

(iii)

or (iv) the radical: 2-oxazolinyl
m is 0 or 1
$R_8$ is H, alkyl, $OR_{11}$, $R_{11}$ being H, alkyl or

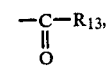

$R_{13}$ being alkyl or aryl or $R_8$ is

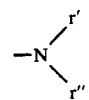

when $m=1$, $r'$ and $r''$ representing H, alkyl mono or polyhydroxyalkyl, aryl or a heterocycle when they are taken together, $R_9$ is H or alkyl, $R_{10}$ is H, alkyl and the acetals of the said compounds,

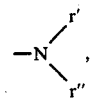

$-OR_{14}$, $R_{14}$ being H, alkyl, mono or polyhydroxyalkyl, aryl or aralkyl a rest of a sugar or represents

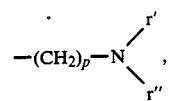

P being 0, 1, 2, or 3
$R_6$ represents a hydrogen atom or a lower alkyl radical,
$R_7$ represents H, alkyl, halogen, hydroxyl, sulfydryl, alkoxy, alkylthio, acyloxy, acylthio, acylamino or primary, secondary or tertrary amino and the salts of said compounds.

These compounds find an application in the cosmetic and pharmaceutical fields.

4 Claims, No Drawings

PHARMACEUTICAL USES OF SUBSTITUTED 6(5,6,7,8)TETRAHYDRO-5,5,8,8-TETRAMETHYL-2-NAPHTHYL)-2-NAPHTHOIC ACID AND ITS ESTERS

The object of this invention concerns polysubstituted naphthalene derivatives, their preparation process and their use in the pharmaceutical and cosmetic fields.

The new polysubstituted naphthalene derivatives are part of a class of compounds known as "retinoids", the best known exponents of which are the trans and cis retinoic acids (tretinoin and isotretinoin), and etretinate.

As compared with retinoids, naphthalene polysubstituted derivatives obtained through this invention have a greater stability to light and oxygen, due to their structure. They are also more effective in the topical and systematic treatment of dermatological ailments linked with keratinization disorders (differentiation/proliferation) and of dermatological or other ailments with anti-inflammatory and/or immuno-allergic components, and they have an anti-tumoral activity as well.

These new naphthalene polysubstituted derivatives can be represented by the following general formula:

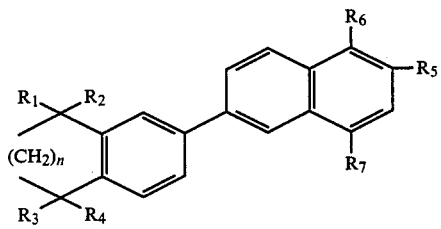

in which:
n is 1 or 2
$R_1$, $R_2$, $R_3$ and $R_4$, identical or different, represent a hydrogen atom or a methyl radical,
$R_5$ represents:
(i) the radical:

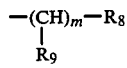

(ii) the radical:

(iii) the radical:

(iv) the radical: 2-oxazolinyl
in which:
m is 0 or 1
R represents:
(a) a hydrogen atom,
(b) a lower alkyl radical
(c) a radical $—OR_{11}$, $R_{11}$ representing a hydrogen atom, a lower alkyl radical, a

radical, $R_{13}$ representing an alkyl radical having from 1 to 20 carbon atoms or an aryl radical, or
(d) a

radical when m=1, r' and r" representing a hydrogen atom, a lower alkyl radical, a mono or polyhydroxy alkyl radical, an aryl radical eventually substituted or taken together form an heterocycle,
$R_9$ represents a hydrogen atom or a lower alkyl radical,
$R_{10}$ represents a hydrogen atom; a lower alkyl radical and the corresponding acetals of the said carbonyl compounds; a

radical, r' and r" having the same meanings as above where r' represents a hydrogen atom and r" represents a residue of amino-acid or glucosamine; a $—OR_{14}$, radical, $R_{14}$ representing a hydrogen atom, an alkyl radical having from 1 to 20 carbon atoms, a mono or polyhydroxy alkyl, aryl or aralkyl radical eventually substituted, a residue of a sugar, or represents the radical

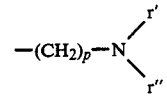

p being 0, 1, 2 or 3 and r' and r" having the same meanings as above,
$R_6$ represents a hydrogen atom or a lower alkyl radical and
$R_7$ represents a hydrogen atom, a lower alkyl radical, a halogen atom, hydroxyl, a sulfhydryl radical, a lower alkoxy, a lower thioalkyl, a lower acyloxy, thioacyl or aminoacyl radical, or a primary, secondary or tertiary amino radical,
and the salts of the said compounds of Formula (I), excluding those compounds of Formula (I) in which $R_6$=H and $R_7$=H or a halogen atom simultaneously.

The expression "lower alkyl radical" designates radicals having from 1 to 6 carbon atoms, in particular methyl, ethyl, isopropyl, butyl and t-butyl radicals.

"Lower alkoxy, lower thioalkyl, and lower acyloxy, thioacyl or aminoacyl radicals" are radicals having from 1 to 4 carbon atoms.

"Mono-hydroxyalkyl radicals" are radicals having 2 to 3 carbon atoms, notably 2-hydroxy ethyl and 2-hydroxy propyl radicals.

"Polyhydroxyalkyl radicals" are radicals having from 3 to 6 carbon atoms and from 2 to 5 hydroxyl groups such as 2,3-dihydroxypropyl, 2,3,4-trihydroxybutyl and 2,3,4,5-tetrahydroxypentyl.

An aryl radical is a phenyl radical eventually substituted by a halogen atom, a hydroxyl or a nitro function.

As preferred aralkyl radicals, the benzyl and phenethyl radicals may be mentioned.

When the r' and r" radicals taken together form a heterocycle, the latter may by a piperidino, piperazino, morpholino or pyrrolidino radical.

When the $R_{10}$ radical represents a hydrogen atom or a lower alkyl, acetals are lower dialkylacetals such as dimethyl- or diethylacetals.

The expression "residue of a sugar" means a radical derived from a sugar such as glucose, mannitol or pentaerythritol.

Among Formula (I) compounds, the following may be mentioned:
4-hydroxy-6-(5,6,7,8-tetrahydro-5,5,8,8tetramethyl-2-naphthyl)2-naphthoic acid; 4-methoxy-6-(5,6,7,8-tetrahydro-5,5,8,8-tetramethyl-2-naphthyl)-2-naphthoic acid; 4-acetoxy-6-(5,6,7,8-tetrahydro-5,5,8,8-tetramethyl-2-naphthyl)-2-methyl naphthoate; 4-acetoxy-1-methyl-6-(5,6,7,8-tetrahydro-5,5,8,8-tetramethyl-2-naphthyl)-2-methyl naphthoate; 4-hydroxy-1-methyl-6-(5,6,7,8-tetrahydro-5,5,8,8-tetramethyl-2-naphthyl)-2-naphthoic acid; 4-hydroxy-1-methyl-6-(5,6,7,8-tetrahydro-5,5,8,8-tetramethyl-2-naphthyl)-2-methylnaphthoate; 4-mercapto-1-methyl-6-(5,6,7,8-tetrahydro-5,5,8,8-tetramethyl-2-naphthyl)-2-naphthoic acid; 1-methyl-6-(5,6,7,8-tetrahydro-5,5,8,8-tetramethyl-2-naphthyl)-2-naphthoic acid; 1-methyl-6-(5,6,7,8-tetrahydro-5,5,8,8-tetramethyl-2-naphthyl)-2-naphthalene methanol; 1-methyl-6-(5,6,7,8-tetrahydro-5,5,8,8-tetramethyl-2-naphthyl)-2-naphthaldehyde; α-methyl[-1-methyl-6-(5,6,7,8-tetrahydro-5,5,8,8-tetramethyl-2-naphthyl)]-2naphthalene methanol; α-ethyl-[1methyl-6-(5,6,7,8-tetrahydro-5,5,8,8-tetramethyl-2-naphthyl)]-2-naphthalene methanol; α-n-propyl[-1-methyl-6-(5,6,7,8-tetrahydro-5,5,8,8-tetramethyl-2-naphthyl)]-2-naphthalene methanol; methyl,1-methyl-6-(5,6,7,8-tetrahydro-5,5,8,8tetramethyl-2-naphthyl)-2-naphthylmethyl ether; ethyl,1-methyl-6-(5,6,7,8-tetrahydro-5,5,8,8-tetramethyl-2-naphthyl)2-naphthylmethyl ether; methyl,1-methyl-6-(5,6,7,8-tetrahydro-5,5,8,8-tetramethyl-2-naphthyl)-2-naphthyl ketone; ethyl,1-methyl-6-(5,6,7,8-tetrahydro-5,5,8,8-tetramethyl -2-naphthyl)-2-naphthyl ketone; 1-methyl-6-(5,6,7,8-tetrahydro-5,5,8,8-tetramethyl-2-naphthyl)-2-naphthylmethyl acetate; 1-methyl-6-(5,6,7,8-tetrahydro-5,5,8,8-tetramethyl-2-naphthyl)-2-naphthylmethyl propionate; α-methyl-[1-methyl-6-(5,6,7,8-tetrahydro-5,5,8,8-tetramethyl-2-naphthyl)]-2-naphthylmethyl acetate; and α-methyl[α-1methyl-6-(5,6,7,8-tetrahydro-5,5,8,8-tetramethyl-2-naphthyl)]-2-naphthylmethyl propionate.

Formula (I) preferred compounds, according to the invention, are those corresponding to the following formula:

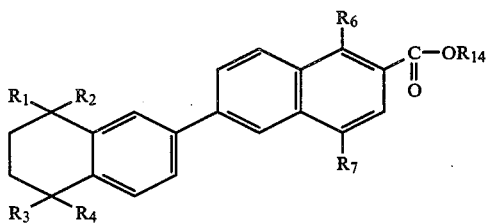

in which:
$R_1$, $R_2$, $R_3$, and $R_4$ represent a methyl radical,
$R_{14}$ represents a hydrogen atom or a lower alkyl radical,
$R_6$ represents a hydrogen atom or a methyl radical, and
$R_7$ represents an acetoxy, methoxy, hydroxy, sulfhydryl radical or a hydrogen atom when $R_6$ represents a methyl radical.

Among these compounds, the following can be mentioned in particular:
4-hydroxy-6-(5,6,7,8-tetrahydro-5,5,8,8-tetramethyl-2-naphthyl)-2-naphthoic acid; 4-methoxy-6-(5,6,7,8-tetrahydro-5,5,8,8-tetramethyl-2-naphthyl)-2-naphthoic acid; 4-acetoxy-1-methyl-6-(5,6,7,8-tetrahydro-5,5,8,8tetramethyl-2-naphthyl)-2-methyl naphthoate; 4-acetoxy-1-methyl-6-(5,6,7,8-tetrahydro-5,5,8,8-tetramethyl-2-naphthyl)-2-methyl naphthoate; 4-hydroxy-1-methyl-6-(5,6,7,8-tetrahydro-5,5,8,8-tetramethyl-2-naphthyl)-2-naphthyl)-2-naphthoic acid; 4-hydroxy-1-methyl-6-(5,6,7,8-tetrahydro-5,5,8,8tetramethyl-2-naphthyl)-2-methyl naphthoate; 4-mercapto-1-methyl-6-(5,6,7,8-tetrahydro-5,5,8,8-tetramethyl-2-naphthyl-2-naphthoic acid; and 1-methyl-6-(5,6,7,8-tetrahydro-5,5,8,8-tetramethyl-2-naphthyl)-2-naphthoic acid.

The compounds in this invention are obtained through a coupling reaction between a halogen compound corresponding to Formula (II) and a halogen derivative of naphthalene corresponding to Formula (III):

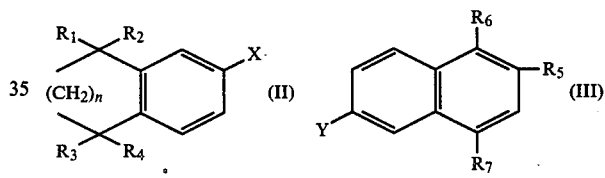

in which $R_1$ to $R_7$ and n have the same meanings as those given above for Formula (I) and X and Y represent Cl, Br, F or I.

With this coupling process, the Formula (II) halogen compound is transformed into its magnesium, lithium or zinc derivative according to known recorded methods and it is bonded to the Formula (III) halogen derivative of naphthalene, using as a catalyst for the reaction a transition metal or one of its complexes.

As catalysts, those derived from nickel or palladium may be mentioned in particular, especially the complexes of $Ni^{II}(NiCl_2)$ with various phosphines.

The coupling reaction usually occurs at a temperature between $-20°$ and $+30°$ C. in an anhydrous solvent such as, for example, dimethylformamide or tetrahydrofurane.

The product obtained can be purified by recrystallization or by chromatography on silica column.

Obviously, the Formula (III) halogen derivative of naphthalene selected for the coupling reaction with the Formula (II) halogen compound must be such as to lead, through subsequent reaction, to the various meanings of the $R_5$ radical.

Among particularly appropriate Formula (III) halogen derivatives of naphthalene are 4-acetoxy 6-bromo 2-methyl naphthoate and 4-acetoxy 6-bromo 1-methyl 2-methyl naphthoate.

Formula (II) halogen compounds are for the most part well known and have been described in U.S. Pat.

No. 3,499,751, in particular those in which n=2, i.e. 2-chloro or 2-bromo-5,6,7,8 tetramethyl-5,5,8,8-tetrahydronaphthalene.

When the compounds in this invention are in the form of salts, they may be either salts of an alkali or alkaline earth metal or an organic amine when they include at least one free acid function, or salts of a mineral or organic acid, in particular of hydrochlorides, hydrobromides or citrates, when they include at least one amine function.

Another object of this invention is the Formula (I) compounds and/or one of their salts defined above, as medicines.

These compounds prove to be quite active in the decarboxylase ornithin inhibition test after induction by tape stripping, in the rat. This test is accepted as a measure of the retinoids' action on cellular proliferation phenomena.

They also show improved activity in the differentiation test of F9 embryonic teratocarcinoma cells (Cancer Research 43, pages 5268, 1983).

These compounds are particularly suited for the treatment of dermatological ailments linked with a keratinization disorder (differentiation, proliferation) as well as dermatological or other ailments with an inflammatory component, in particular:

ordinary acne, comedonian or polymorphic, solar senile acne, and professional or medicine-induced acnes, extensive and/or severe forms of psoriasis, and other keratinization problems, in particular ichthyosis and ichthyosis-like states, Darier's disease, Palmo-plantar keratodermatosis, leukoplasia and leukoplasia-like states, all dermatological proliferations whether benign or malignant, severe or extensive.

They also have an action on certain rheumatoid ailments, in particular psoriatic rheumatism.

The object of this invention, therefore, is also medicinal preparations including at least one Formula (I) compounds and/or one of its salts as defined above.

The object of this invention, therefore, is also a new medicinal preparation designed in particular for the treatment of the above-mentioned ailments, characterized by the fact that it includes at least one Formula (I) compound, in an acceptable pharmaceutical base.

As previously indicated, derivatives obtained through this invention offer greater stability to light and oxygen, as compared to the usual retinoids, due essentially to the fact that they do not contain a double bond that can easily form isomers.

On the other hand, the irritation test done on rabbits showed that Formula (I) compounds were less irritating than retinoic acid.

Compounds obtained through the invention process are generally administered on the basis of a daily dose of approximately from 2 $\mu$g/Kg to 2 mg/Kg and preferably from 10 to 100 $\mu$g/Kg.

As a base for the preparations, any conventional excipient can be used, the active compound being in a state either dissolved or dispersed through the vehicle.

The medicine can be administered enterally, parenterally or topically. Enterally, medicines can be in the form of tablets, capsules, pills, syrups, suspensions, solutions, powders, granules or emulsions. Parenterally, the preparations can be in the form of solutions for perfusion or for injection.

For topical administration, the pharmaceutical preparations based on the compounds obtained according to the invention are in the form of liniments, tinctures, creams, solutions, lotions, gels, ointments, powders, impregnated stamps or pads, sprays, or even, suspensions.

Topical preparations contain preferably from 0.0005 to approximately 5% by weight of the Formula (I) compound.

These topical preparations can either by anhydrous or aqueous depending on clinical requirements and may contain other ingredients.

Formula (I) compounds and/or their salts obtained according to the invention have also an application in the field of cosmetics, in particular for capillary and bodily hygiene and notably against acne, for promoting hair growth and preventing hair fall, for fighting the greasy appearance of the skin or hair, or for protection against the ill-effects of sun exposure, or still to combat the skin's physiological dryness.

This invention, therefore, aims also at achieving a cosmetic preparation containing, in an acceptable cosmetic base, at least one Formula (I) compound, such preparation taking, in particular, the form of a lotion, gel, soap or shampoo.

The concentration in Formula (I) compound(s) in cosmetic preparations is from 0.0005 to 2% by weight, preferably from 0.01 to 1% by weight.

Medicinal and cosmetic preparations obtained according to this invention may contain inert additives or even pharmacodynamically or cosmetically active additives, in particular: moisturizing agents such as thiamorpholinone and its derivatives or urea, anti-seborrheic agents such as S-carboxymethylcystine, S-benzyl-cystamine and their derivatives, tioxolone, antibiotics such as erythromycin, neomycin and tetracyline; agents promoting hair growth, such as "Minoxidil" (diamino-2,4 piperidino-6 pyrimidine oxyde-3) and its derivatives; anthalin and its derivatives; Diasoxide, Phenytoin and oxapropanium iodide; steroid and non-steroid anti-inflammatory agents; carotenoids and, in particular, -carotene; antipsoriasis agents such as anthralin and its derivatives, eicosatetraynoic 5,8,11,14 acid and eicosatriynoic 5,8,11 acid.

Preparations obtained according to this invention may also contain flavor-improving agents, preserving agents, stabilizing agents, moisture-regulating agents, pH-regulating agents, osmotic pressure modifying agents, emulsifying agents, UV-A and UV-B filters, anti-oxidizing agents such as $\alpha$-tocopherol, butylhydroxyanisole or butylhydroxy toluene.

As an illustration, the following non-restrictive examples of preparation of Formula (I) active compounds obtained according to this invention are given:

EXAMPLE 1 methyl 4-acetoxy-6-(5,6,7,8-tetrahydro-5,5,8,8-tetramethyl-2-naphthyl)-2-naphthoate 4.54 g (17 mmoles) of 5,6,7,8-tetrahydro-5,5,8,8-tetramethyl-2-bromo naphthalene are dissolved into 30 ml of tetrahydrofurane (THF) and treated with 0.62 g (25.5 mmoles) of magnesium. When the magnesium is formed, it is cooled at 20° C. and 2.3 g (17 mmoles) of anhydrous zinc chloride (ZnCl$_2$) are added. After stirring for one hour at room temperature, 3.23 g (10 mmoles) of 4-acetoxy-6-bromo-2-methyl naphthoate and the

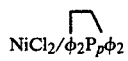

(90 mg, 0.17 mmole) complex are added. After stirring for one hour and then pouring into water (100 ml), extraction is performed with dichloromethane (2×100 ml). The organic phase of the product is washed with a solution saturated with sodium bicarbonate, then with water until neutral, then dried and evaporated. In that manner are obtained 2.50 g (58%) of methyl 4-acetoxy-6-(5,6,7,8-tetrahydro-5,5,8,8-tetramethyl-2-naphthyl)-2-naphthoate
which melts at 201° C.

EXAMPLE 2

4-hydroxy-6-(5,6,7,8-tetrahydro-5,5,8,8-tetramethyl-2-naphthyl)-2naphthoic acid 1.7 g (3.95 mmoles) of ester obtained in Example 1 are added to a mixture of 100 ml of methanolic soda (2M) and 50 ml of water. The mixture is heated for 4 hours, evaporated dry, and, after 100 ml of water are added, extracted with ether (300 ml). The aqueous phase of the product is recuperated, brought to pH 1 with concentrated hydrochloric acid. After extraction of the precipitate with ether (300 ml), it is washed in water until neutral, then dried and evaporated. The solid obtained is recrystallized in acetonitrile. Thus is obtained 1.3 g (88%) of 4-hydroxy-6-(5,6,7,8-tetrahydro-5,5,8,8-tetramethyl-2-naphthyl)-2-naphthoic acid which melts at 299° C.

EXAMPLE 3

4-methoxy-6-(5,6,7,8-tetrahydro-5,5,8,8-tetramethyl-2-naphthyl)-2-naphthoic acid 0.8 g (2.1 mmoles) of the acid obtained in Example 2, dissolved in 10 ml of THF, are added drop by drop to a suspension of sodium hydride (0.113 g; 4.7 mmoles) in 10 ml of THF. After stirring for two hours at room temperature, 10 ml of dimethylformamide and 0.90 g (6.3 mmoles) of methyl iodide are added. After stirring for one hour, the mixture is poured into water and brought to pH 1 (concentrated hydrochloric acid). Following extraction by ether, the organic phase is decanted, then dried and evaporated. The solid thus formed is recrystallized in a mixture of diisopropyl ether (50%) and cyclohexane (50%). In this manner is obtained 0.60 g (74%) of 4-methoxy-6-(5,6,7,8-tetrahydro-5,5,8,8-tetramethyl-2-naphthyl)-2 naphthoic acid which melts at 242° C.

EXAMPLE 4 methyl 4-acetoxy-1-methyl-6-(5,6,7,8-tetrahydro-5,5,8,8-tetramethyl-2-naphthyl)-2-naphthoate (a) Preparation of 4-methyl 4-acetoxy-6-bromo-1-methyl-2-naphthoate A solution of p-bromo-acetophenone (19.9 g; 100 mmoles) and methyl succinate (17.6 g; 120 mmoles) is added drop by drop in 40 ml of tertbutanol to a suspension of tert-butylate of potassium (12.4 g, 110 mmoles) in the tertbutanol (50 ml). The mixture is heated for three hours by retort, then acidified to pH 4 with concentrated HCl. Dry evaporation and extraction by ether follow. The product is washed with water, then extracted with a solution of sodium carbonate, acidified and extracted with ether. It is dried and evaporated. A solid is obtained which is recrystallized in the cyclohexane. Thus is obtained 21.9 g (70%) of 5-p-bromophenyl-3-carbethoxy-5-methyl-3-pentenoic acid which melts at 107° C. That acid (21.7 g; 69.3 mmoles) is heated by retort in a mixture of acetic anhydride (90 ml) and sodium acetate (11 g). After 3 hours, dry evaporation is effected, followed with extraction by ether. The organic phase is washed successively with water, a solution of sodium bicarbonate, then again with water. It is dried and evaporated. Thus is obtained an oil which crystallizes from cyclohexane. And thus is obtained 4-acetoxy-6-bromo-1-methyl-2-methyl naphthoate which melts at 78° C.

(b) methyl 4-acetoxy-1-methyl-6-(5,6,7,8-tetrahydro-5,5,8,8-tetramethyl-2-naphthyl)-2-naphthoate In the same manner as in Example 1, starting with 3.4 g (10 mmoles) of methyl 4-acetoxy-6-bromo-1-methyl-2-naphthoate, 1.6 g (36%) of methyl 4-acetoxy-1-methyl-6-(5,6,7,8-tetrahydro-5,5,8,8-tetramethyl-2-naphthyl)-2-naphthoate which melts at 170° C. is obtained.

EXAMPLE 5

4-hydroxy-1-methyl-6-(5,6,7,8-tetrahydro-5,5,8,8-tetramethyl-2-naphthyl-2-naphthoic acid In the same manner as in Example 2, starting with 1.3 g (2.9 mmoles) of the ester described in Example 4, 0.70 g (64%) of 4-hydroxy-1-methyl-6-(5,6,7,8-tetrahydro-5,5,8,8-tetramethyl-2-naphthyl)-2-naphthoic acid which melts at 266° C. is obtained.

EXAMPLE 6 methyl 4-hydroxy-1-methyl-6-(5,6,7,8-tetrahydro-5,5,8,8-tetramethyl-2-naphthyl)-2-naphthoate 8.1 g (0.0209 mole) of the acid obtained in Example 5, 100 ml of methanol and 0.6 ml (0.0105 mole) of concentrated sulfuric acid are introduced in a balloon-flask, then heated by retort for 8 hours. After dry evaporation, water is added, neutralization is effected with sodium bicarbonate, followed with extraction with dichloromethane. After drying the organic phase on magnesium sulfate, the resulting solid is evaporated and then recrystallized in acetonitrile. Yield: 7.6 g (90.5%), fusion temperature: (224°–225° C.). RF:0.5 [Merck silica plaques, the eluent being a mixture of ether-hexane (50:50)]

EXAMPLE 7

4-mercapto-1-methyl-6-(5,6,7,8-tetrahydro-5,5,8,8-tetramethyl-2-naphthyl)-2-naphthoic acid Preparation of 4-(dimethylamino thiocarbonyloxy)-1-methyl-6-(5,6,7,8-tetrahydro-5,5,8,8-tetramethyl-2-naphthyl)-2-methyl naphthoate.

(a) In a balloon-flask 1.9 g (0.064 mole) of sodium hydride at 80% is introduced in 50 ml of dimethyl formamide (DMF). Drop by drop, 21.5 g (0.0534 mole) of the ester obtained in Example 6 are added to 50 ml of DMF then stirred for one hour at room temperature. Then, 9.3 g (0.0748 mole) of dimethyl thiocarbamoyl chloride are added to 50 ml of DMF and stirred for two hours at room temperature. The product is poured into 300 ml of HCl 1N, extracted with ethyl ether, the organic phase is decanted, washed with water to which sodium bicarbonate has been added, dried on magnesium sulfate and then evaporated.

After recrystallization in the hexane-cyclohexane mixture, 23 g of the expected product are obtained (88%), with a fusion temperature of 142°–143° C.

RF: 0.5 (MERCK silica plaques, the eluent being dichloromethane).

Preparation of 4-(dimethylamino carbonylthio)-1-methyl-6-(5,6,7,8-tetrahydro-5,5,8,8-tetramethyl-2-naphtyl)-2-methyl naphthoate.

(b) In a balloon-flask under nitrogen, 23 g (0.047 mole) of the ester obtained above are introduced and heated at 260° C. for 15 minutes. Then, the product is dissolved in the minimum quantity of dichloromethane and chromatography on silica column is effected with dichloromethane as the eluent. In this manner, 18.2 g of the expected intermediate are obtained (79.2%).

RF: 0.45 (MERCK silica plaques, dichloromethane being the eluent).

(c) In a balloon-flask, 18.2 g (0.0372 mole) of the preceeding ester and 400 ml of methanolic soda 2N are introduced. They are heated by retort for 8 hours, then evaporated dry. Water is added to the residue, then it is acidified to pH 1 with concentrated HCl and extracted with ethyl ether. After decanting the organic phase, it is dried on magnesium sulfate. After evaporation and recrystallization in acetonitrile, 11.5 g of the expected product (76%) are obtained.

RF: 0.25 (MERCK silica plaques, ether being the eluent).

EXAMPLE 8

1-methyl-6-(5,6,7,8-tetrahydro-5,5,8,8-tetramethyl-2-naphthyl)-2-naphthoic acid

In a balloon-flask, 11.5 g (0.0284 mole) of the acid obtained in Example 7 and 300 ml of ethyl alcohol are introduced. Under nitrogen, 40 g of Raney nickel are added and the contents are heated for two hours by retort. The catalyst is filtered, the alcoholic phase is evaporated, then the resulting solid is chromatographed on silica column using an ether-hexane mixture (80:20).

After recrystallization in acetonitrile, 5.4 g of the expected product are obtained, with a fusion temperature of 243°–244° C. (Yield 52%)—RF: 0.2 (MERCK silica plaques, ether being the eluent).

EXAMPLES OF COMPOSITIONS

Example 1

| 0.2 g Tablet | |
|---|---|
| Compound from example 2 | 0.001 g |
| Starch | 0.114 g |
| Dicalcium phosphate | 0.020 g |
| Silica | 0.020 g |
| Lactose | 0.030 g |
| Talcum | 0.010 g |
| Magnesium stearate | 0.005 g |

In this example, the compound from example 2 may be replaced with the same quantity of the compound from example 8.

Example 2

| 0.5 g Capsule - Powder formula | |
|---|---|
| Compound from example 2 | 0.001 g |
| Corn starch | 0.150 g |
| Magnesium stearate | 0.250 g |
| Saccharose QSP | 0.500 g |

The powder is packaged in a capsule made of gelatin and titanium dioxide.

Example 3

| Liniment | |
|---|---|
| Compound from example 5 | 0.001 g |
| Stearyl alcohol | 3.000 g |
| Lanolin | 5.000 g |
| Vaseline | 15.000 g |
| Distilled water QSP | 100.000 g |

In this example, the compound from example 5 may be replaced with an equal quantity of the compound from example 8.

Example 4

| Gel | |
|---|---|
| Compound from example 5 | 0.005 g |
| Hydroxy-propyl cellulose sold by the Hercules Company under the name of "Klucel HF" | 2.000 g |
| Water:ethanol (50:50) QSP | 100.000 g |

Example 5

| Non-ionic oil-in-water cream | |
|---|---|
| Compound from example 5 | 0.050 g |
| Cetyl alcohol | 3.000 g |
| Stearyl alcohol | 3.400 g |
| Oxyethylated cetyl alcohol (20 moles) | 0.630 g |
| Oxyethylated stearyl alcohol (20 moles) | 1.470 g |
| Glycerol monostearate | 2.000 g |
| Vaseline oil | 15.000 g |
| Glycerin | 10.000 g |
| Preservatives | qs |
| Distilled water QSP | 100.000 g |

Example 6

| Liniment | |
|---|---|
| Compound from example 5 | 0.020 g |
| Isopropyl myristate | 81.700 g |
| Fluid vaseline oil | 9.100 g |
| Silica sold by the Degussa Company under the name of "AEROSIL 200" | 9.180 g |

What is claimed is:

1. A process for the treatment of dermatological ailments linked to a keratinization disorder comprising administering to a patient suffering from said disorder a compound of the formula

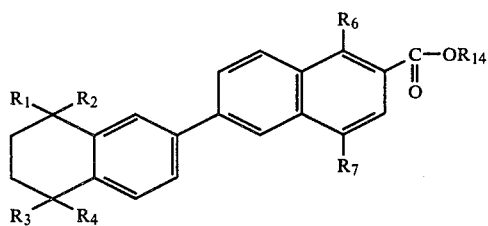

wherein

R$_1$, R$_2$, R$_3$ and R$_4$ represent methyl,

R$_{14}$ represents hydrogen or lower alkyl,

R$_6$ represents hydrogen or methyl, and

R$_7$ represents acetoxy, methoxy, hydroxy or sulfhydryl radical, or hydrogen when R$_6$ represents methyl, at a daily dose ranging from 2 μg/kg to 2 mg/kg.

2. A process for the treatment of dermatological ailments linked to a keratinization disorder comprising topically applying to the area of the skin of a patient affected by such a disorder a pharmaceutical composition comprising in a pharmaceutically acceptable carrier suitable for topical application to the skin, 0.0005 to 5 percent by weight of said composition of a compound having the formula

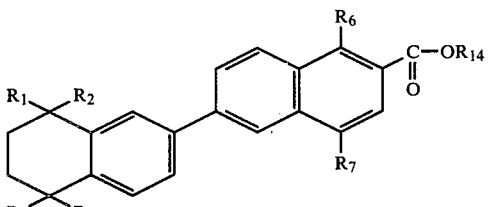

wherein

R$_1$, R$_2$, R$_3$ and R$_4$ represent methyl,

R$_{14}$ represents hydrogen or lower alkyl,

R$_6$ represents hyrogen or methyl and

R$_7$ represents acetoxy, methoxy, hydroxy or sulfhydryl radical, or hydrogen when R$_6$ represents methyl.

3. The process of claim 2 wherein said compound is 1-methyl-6-(5,6,7,8-tetrahydro-5,5,8,8,-tetramethyl-2-naphthyl)-2-naphtoic acid.

4. The process of claim 2 wherein said compound is selected from the group consisting of
(1) 6-(5,6,7,8-tetrahydro-5,5,8,8-tetramethyl-2-naphthyl)-4-hydroxy-2-naphthoic acid,
(2) 6-(5,6,7,8-tetrahydro-5,5,8,8,-tetramethyl-2-naphthyl)-4-methoxy-2-naphthoic acid,
(3) methyl 6-(5,6,7,8-tetrahydro-5,5,8,8,-tetramethyl-2-naphthyl)-4-acetoxy-2-naphthoate,
(4) methyl 6-(5,6,7,8-tetrahydro-5,5,8,8,-tetramethyl-2-naphthyl)-4-acetoxy-1-methyl-2-naphthoate,
(5) 6-(5,6,7,8-tetrahydro-5,5,8,8,-tetramethyl-2-naphthyl)-4-hydroxy-1-methyl-2-naphthoic acid,
(6) methyl 6-(5,6,7,8-tetrahydro-5,5,8,8,-tetramethyl-2-naphthyl)-4-hydroxy-1-methyl-2-naphthoate,
(7) 6-(5,6,7,8-tetrahydro-5,5,8,8,-tetramethyl-2-naphthyl)-4-mercapto-1-methyl-2-naphthoic acid, and
(8) 6-(5,6,7,8-tetrahydro-5,5,8,8,tetramethyl-2-nahthyl)-1-methyl-2-naphthoic acid.

* * * * *

UNITED STATES PATENT AND TRADEMARK OFFICE
CERTIFICATE OF CORRECTION

PATENT NO. : 4,666,941

DATED : May 19, 1987

INVENTOR(S) : SHROOT, et al

It is certified that error appears in the above-identified patent and that said Letters Patent is hereby corrected as shown below:

On the Title Page:

IN THE HEADING

[73] Assignee, should read --Groupement Economique dit:

Centre International De Recherches Dermatologiques

C.I.R.D., Valbonne, France--.

Signed and Sealed this

Thirteenth Day of December, 1988

*Attest:*

DONALD J. QUIGG

*Attesting Officer*  *Commissioner of Patents and Trademarks*